United States Patent [19]

Conine

[11] 4,195,078

[45] Mar. 25, 1980

[54] NABILONE GRANULATION

[75] Inventor: James W. Conine, Indianapolis, Ind.

[73] Assignee: Eli Lilly and Company, Indianapolis, Ind.

[21] Appl. No.: 19,810

[22] Filed: Mar. 9, 1979

[51] Int. Cl.$^2$ .............................................. A61K 31/79
[52] U.S. Cl. ..................................... 424/80; 424/283
[58] Field of Search ................................. 424/80, 283

[56] References Cited

U.S. PATENT DOCUMENTS

| | | | |
|---|---|---|---|
| 3,136,692 | 6/1964 | Bandelin | 424/80 |
| 3,632,778 | 1/1972 | Sheth et al. | 424/80 X |
| 3,655,870 | 4/1972 | Mueller | 424/80 |
| 3,851,032 | 11/1974 | Andrews et al. | 424/80 X |
| 3,920,809 | 11/1975 | Thakkar | 424/80 |
| 3,932,615 | 1/1976 | Ito et al. | 424/80 |
| 3,987,188 | 10/1976 | Archor et al. | 424/283 |
| 4,024,275 | 5/1977 | Archor et al. | 424/283 |
| 4,087,545 | 5/1978 | Archor etal. | 424/283 |
| 4,087,546 | 5/1978 | Archor et al. | 424/283 |
| 4,087,547 | 5/1978 | Archor et al. | 424/283 |
| 4,088,777 | 5/1978 | Archor et al. | 424/283 |
| 4,143,129 | 3/1979 | Marsden | 424/80 |

FOREIGN PATENT DOCUMENTS 885974 11/1971 Canada ..................................... 424/80

1467792 12/1968 Fed. Rep. of Germany ............. 424/80

OTHER PUBLICATIONS

Thakker et al. J. Pharm. Pharmacol. 29(12): 783-784 (1977) "Solid Dispersion Approach for Overcoming Bioavailability Problems due to Polymorphism of Nabilone, a Cannabinoid Derivative".

Rubin et al. Clin. Pharmacol. Ther. 1977: 22(1): 89-91 "Physiologic Disposition of Nabilone, a Cannabinol Derivative, in Man".

Newton, J. M. et al. J. Pharm. Pharmacol 1977: 29(5): 294-297 The Influence of Additions on the Presentation of a Drug in Hard Gelatin Capsules.

Doelker et al. J. Pharm. Pharmacol. 29(4):193-198 (1977) The Effect of Some Binding Agents on Mechanical Properties of Granules.

Lemberger et al. Cli. Pharmacol. 18(6): 720-726 (1975) Clinical Pharmacology of Nabilone, a Cannabinol Derivative.

*Primary Examiner*—Shep K. Rose
*Attorney, Agent, or Firm*—James L. Rowe; Arthur R. Whale

[57] ABSTRACT

A solution of nabilone and PVP in anhydrous ethanol is used to granulate ethanol-insoluble pharmaceutically-acceptable excipients such as starch.

2 Claims, No Drawings

NABILONE GRANULATION

BACKGROUND OF THE INVENTION

Nabilone [trans-dl-1-hydroxy-3-(1',1'-dimethylheptyl)-6,6-dimethyl-6a,7,8,9,10,10a- hexahydrobenzo[b,d]pyran-9-one] is encompassed within a group of useful intermediates prepared by Farenholtz, et al., *J. Am. Chem. Soc.*, 88, 2079 (1966), 89, 5934 (1967) for the preparation of $\Delta^9$-THC (tetrahydrocannibinol) and its alkylated congeners having alkyl groups of from 1 to 10 carbon atoms at C-3. ($\Delta^9$-THC is trans-dl-1-hydroxy-3-n-pentyl-6,6,9-trimethyl-6a,7,8,10a-tetrahydrobenzo-[b,d]pyran). Archer, U.S. Pat. Nos. 3,928,598, 3,953,603, 3,946,673 and 3,987,188 disclosed that nabilone, in addition to being a "useful intermediary", had activity as an anti-depressant, anti-anxiety, analgesic and/or sedative drug, and Archer and Lemberger further extended its useful actions to that of anti-emetic and for the treatment of glaucoma, U.S. Pat. Nos. 4,087,545 and 4,087,547. Nabilone is not well absorbed from the intestine upon oral administration. Thakker, et al., *J. Pharm. Pharmac.*, 29, 783 (1977) describe some useful formulations for nabilone including a dispersion in polyvinylpyrrolidinone. Thakker, et al. mix nabilone with PVP in a ratio of 1:2–20 in a solvent such as ethanol and then remove the solvent by evaporation in vacuo. The product thus obtained is a glassy solid which must first be broken up and then reduced to a fine powder in order to disperse it uniformally in other pharmaceutical excipients prior to filling into telescoping gelatin capsules.

It is an object of this invention to provide a granulation formulation for nabilone which avoids the inconvenience and difficulties of the aforesaid Thakker et al solid dispersion.

SUMMARY OF THE INVENTION

In fulfillment of the above and other objects, I employ a solution of nabilone and polyvinylpyrrolidone in ethanol as a granulating solution. This solution is then used to granulate pharmaceutical excipients and carriers such as starch, lactose, cellulose and the like. After drying and grinding, the powdered granular material is suitable for blending with other materials to make a formulation suitable for filling into telescoping gelatin capsules as provided. In other words, the nabilone-PVP dispersion of Thakker et al. (loc. cit.) is formed in situ as a granulation for excipients which are insoluble in ethanol. The ratio of nabilone to PVP contains, in my novel granulation as in the Thakker et al. dispersions, one part of nabilone to 2 to 20 parts of PVP.

A granulation thus prepared is shown to have excellent stability as regards nabilone, and dissolution data has shown that the granulation is equivalent to the Thakker et al. dispersion prepared as a glass in the rotary evaporator and then powdered. Equivalent bioavailability has been demonstrated in dogs for the granulation of this invention as compared with the Thakker et al. dispersion.

Other nabilone dispersions prepared by Thakker, et al., including one in polyethylene glycol, can be prepared similarly in situ on the particular excipient using our novel process as described for the nabilone-PVP dispersion above; solution in ethanol followed by granulation of an ethanol-insoluble excipient.

This invention is further illustrated by the following specific example.

EXAMPLE 1

Five grams of nabilone were dissolved in 125 ml. of anhydrous ethanol 0.45 g. of polyvinylpyrrolidone (PVP) were dissolved therein. The resulting viscous solution was added to 450 g. of starch flowable powder in a Hobart mixer. A small amount of additional anhydrous ethanol was used to rinse the nabilone-PVP solution into the mixer. After thorough mixing, the granulation was wet screened through a no. 4 screen (a no. 6 screen can also be used). The screened granulation was air dried and then ground to the desired size in a ball mill.

A nabilone-PVP-starch granulation so prepared can be further blended with other excipients to give a final mixture having the desired nabilone concentration for loading into empty telescoping gelatin capsules.

Other ethanol insoluble excipients such as lactose, mannitol and dextrose can be used in place of flowable starch in preparing the above granulation.

I claim:

1. A method of formulating nabilone for oral administration to mammals which comprises dissolving nabilone and polyvinylpyrrolidone or polyethylene glycol in anhydrous ethanol and using the thus-formed viscous solution to granulate a pharmaceutically-acceptable ethanol-insoluble excipient by thoroughly mixing the solution with the excipient, and then drying the thus-formed granulation.

2. A process according to claim 1 in which polyvinylpyrrolidone and nabilone are dissolved in ethanol to form the granulating solution.

* * * * *